(12) United States Patent
Mukai et al.

(10) Patent No.: US 6,891,620 B2
(45) Date of Patent: May 10, 2005

(54) MEASURING PLATE

(75) Inventors: Atsushi Mukai, Kaisei-machi (JP);
Toshihito Kimura, Kaisei-machi (JP)

(73) Assignee: Fuji Photo Film Co., LTD, Kanagawa-ken (JP)

( * ) Notice: Subject to any disclaimer, the term of this patent is extended or adjusted under 35 U.S.C. 154(b) by 318 days.

(21) Appl. No.: 10/288,593

(22) Filed: Nov. 6, 2002

(65) Prior Publication Data

US 2003/0123063 A1 Jul. 3, 2003

(30) Foreign Application Priority Data

Nov. 6, 2001 (JP) ........................................ 2001-340810

(51) Int. Cl.[7] ............................................. G01N 21/55
(52) U.S. Cl. ..................................... 356/445; 250/239
(58) Field of Search .............................. 356/445–448; 350/239, 573; 422/82.08, 82.11; 372/43, 45–46; 382/12–13

(56) References Cited

U.S. PATENT DOCUMENTS

| | | | | |
|---|---|---|---|---|
| 4,595,290 A | * | 6/1986 | Nose et al. | 356/225 |
| 4,889,427 A | * | 12/1989 | Van Veen et al. | 356/445 |
| 5,341,215 A | * | 8/1994 | Seher | 356/445 |
| 6,577,396 B1 | * | 6/2003 | Naya | 356/445 |
| 6,597,456 B2 | * | 7/2003 | Kubo et al. | 356/445 |
| 6,741,352 B2 | * | 5/2004 | Naya | 356/445 |

FOREIGN PATENT DOCUMENTS

JP       6-167443 A1    6/1994

OTHER PUBLICATIONS

Japanese Abstract No. 10300667, dated Nov. 13, 1998.
Japanese Abstract No. 200065729, dated Mar. 3, 2000.
Takayuki Okamoto, "Surface Refracto–Sensor using Evanescent Waves: Principles and Instrumentations" Sprectral Researches, vol. 47, No. 1 1998, pp21.

* cited by examiner

Primary Examiner—Gregory J. Toatley, Jr.
Assistant Examiner—Sang H. Nguyen
(74) Attorney, Agent, or Firm—Sughrue Mion, PLLC

(57) ABSTRACT

A measuring plate for use in a sensor utilizing the phenomenon of attenuation in total internal reflection provides a dielectric block and a film layer and includes a dielectric plate provided with a plurality of recesses each provided with a film layer and holding a sample in contact with the film layer, and a reflecting optical system including a reflecting surface which is formed on the dielectric plate for each of the recesses to cause the light beam emitted from the light source to impinge upon the interface between the film layer of the recess and the dielectric plate and/or to cause the light beam reflected at the interface between the film layer of the recess and the dielectric plate to travel toward a predetermined position.

30 Claims, 7 Drawing Sheets

MEASURING PLATE

BACKGROUND OF THE INVENTION

1. Field of the Invention

Figure 1:
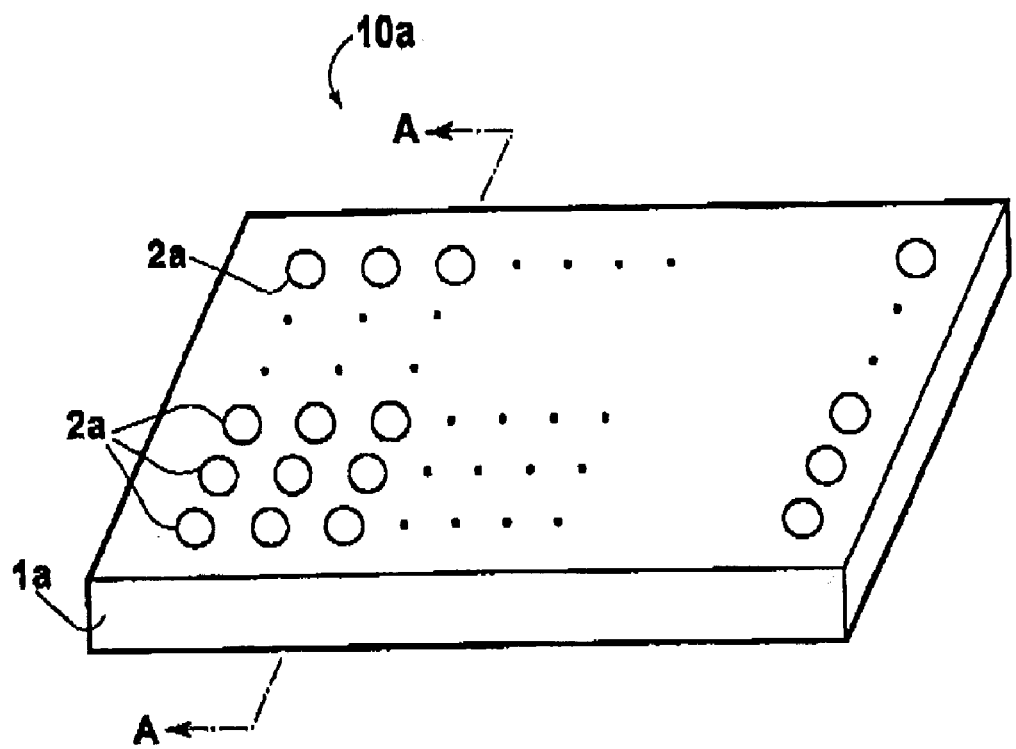

This invention relates to a measuring plate for use in a sensor using attenuation in total internal reflection such as a surface plasmon sensor for quantitatively analyzing a material in a sample on the basis of generation of surface plasmon.

2. Description of the Related Art

In metal, free electrons vibrate in a group to generate compression waves called plasma waves. The compression waves generated in a metal surface are quantized into surface plasmon.

There have been proposed various surface plasmon sensors for quantitatively analyzing a material in a sample utilizing a phenomenon that such surface plasmon is excited by light waves. Among those, one employing a system called "Kretschmann configuration" is best known. See, for instance, Japanese Unexamined Patent Publication No. 6(1994)-167443.

The plasmon resonance sensor using the Kretschmann configuration basically comprises a dielectric block shaped, for instance, like a prism, a metal film which is formed on one face of the dielectric block and is brought into contact with a sample, a light source emitting a light beam, an optical system which causes the light beam to enter the dielectric block to impinge upon the interface of the dielectric block and the metal film at various angles of incidence so that total internal reflection conditions are satisfied at the interface, and a photodetector means which detects the intensity of the light beam reflected in total internal reflection at the interface and detects a state of surface plasmon resonance, i.e., a state of attenuation intotal internal reflection.

In order to obtain various angles of incidence of the light beam to the interface, a relatively thin incident light beam may be caused to impinge upon the interface while deflecting the incident light beam so that the angle of incidence changes or a relatively thick incident light beam may be caused to impinge upon the interface in the form of convergent light or divergent light so that components of the incident light beam impinge upon the interface at various angles. In the former case, the light beam which is reflected from the interface at an angle which varies as the incident light beam is deflected may be detected by a photodetector which is moved in synchronization with deflection of the incident light beam or by an area sensor extending in the direction in which reflected light beam is moved as a result of deflection. In the latter case, an area sensor which extends in directions so that all the components of light reflected from the interface at various angles can be detected by the area sensor may be used.

In such a plasmon resonance sensor, when a light beam impinges upon the interface at a particular angle of incidence θsp not smaller than the angle of total internal reflection, evanescent waves having an electric field distribution in the sample in contact with the metal film are generated and surface plasmon is excited in the interface between the metal film and the sample. When the wave number vector of the evanescent waves is equal to the wave number of the surface plasmon and wave number matching is established, the evanescent waves and the surface plasmon resonate and light energy is transferred to the surface plasmon, whereby the intensity of light reflected in total internal reflection at the interface of the dielectric block and the metal film sharply drops. The sharp intensity drop is generally detected as a dark line by the photodetector.

The aforesaid resonance occurs only when the incident light beam is p-polarized. Accordingly, it is necessary to set the light beam to impinge upon the interface in the form of p-polarized light.

When the wave number of the surface plasmon can be known from the angle of incidence θsp at which the phenomenon of attenuation in total internal reflection (ATR) takes place, the dielectric constant of the sample can be obtained. That is, $$K_{sp}(\omega) = \frac{\omega}{c} \sqrt{\frac{\varepsilon_m(\omega)\varepsilon_s}{\varepsilon_m(\omega) + \varepsilon_s}}$$

wherein $K_{sp}$ represents the wave number of the surface plasmon, ω represents the angular frequency of the surface plasmon, c represents the speed of light in a vacuum, and $\varepsilon_m$ and $\varepsilon_s$ respectively represent the dielectric constants of the metal and the sample.

When the dielectric constant $\varepsilon_s$ of the sample is known, the concentration of the specific material in the sample can be calculated and accordingly a property related to the dielectric constant $\varepsilon_s$ (refractive index) of the sample can be detected by detecting the angle of incidence θsp at which the intensity of light reflected in total internal reflection from the interface of the prism and the metal film sharply drops (this angel θsp will be referred to as "the attenuation angle θsp", hereinbelow).

As a similar apparatus utilizing the phenomenon of attenuation in total internal reflection (ATR), there has been known a leaky mode sensor described in, for instance, "Spectral Research" Vol. 47, No. 1 (1998), pp 21 to 23 & pp 26 and 27. The leaky mode sensor basically comprises a dielectric block shaped, for instance, like a prism, a clad layer which is formed on one face of the dielectric block, an optical waveguide layer which is formed on the clad layer and is brought into contact with a sample, a light source emitting a light beam, an optical system which causes the light beam to enter the dielectric block to impinge upon the interface of the dielectric block and the metal film at various angles of incidence so that total internal reflection conditions are satisfied at the interface and attenuation in total internal reflection takes place due to excitation of a waveguide mode in the optical waveguide layer, and a photodetector means which detects the intensity of the light beam reflected in total internal reflection at the interface and detects a state of waveguide mode excitation, i.e., a state of attenuation in total internal reflection.

In the leaky mode sensor with this arrangement, when the light beam is caused to impinge upon the clad layer through the dielectric block at an angle not smaller than an angle of total internal reflection, only light having a particular wave number and impinging upon the optical waveguide layer at a particular angle of incidence comes to propagate through the optical waveguide layer in a waveguide mode after passing through the clad layer. When the waveguide mode is thus excited, almost all the incident light is taken in the optical waveguide layer and accordingly, the intensity of light reflected in total internal reflection at the interface of the dielectric block and the clad layer sharply drops. That is, attenuation in total internal reflection occurs. Since the wave number of light to be propagated through the optical waveguide layer in a waveguide mode depends upon the refractive index of the sample on the optical waveguide layer, the refractive index and/or the properties of the sample related to the refractive index can be detected on the basis of the angle of incidence at which the attenuation in total internal reflection occurs.

In the conventional surface plasmon resonance sensors or leaky mode sensors, there has been proposed a system in which a plurality of measuring chips are arranged on a plate in order to increase the measuring speed or to automate the measurement.

However, this system is disadvantageous in that it is necessary to transfer the measuring chips from the plate to the sensor one by one. When measurement is performed with the measuring chips held on the plate, the light beam can be eclipsed, for instance, by the bottom portion of an adjacent measuring chip, which deteriorates the accuracy of measurement.

SUMMARY OF THE INVENTION

In view of the foregoing observations and description, the primary object of the present invention is to provide a measuring plate which allows to perform accurate measurement on a plurality of samples held thereon with the samples kept thereon.

In accordance with a first aspect of the present invention, there is provided a measuring plate for use in a sensor utilizing the phenomenon of attenuation in total internal reflection comprising a dielectric block provided with a film layer to be brought into contact with a sample, a light source which emits a light beam, an incident optical system which causes the light beam to enter the dielectric block so that total internal reflection conditions are satisfied at the interface of the dielectric block and the film layer and various angles of incidence of the light beam to the interface can be obtained, and a photodetector means which detects the intensity of the light beam reflected in total internal reflection at the interface and detects a state of attenuation in total internal reflection, the measuring plate being for providing the dielectric block and the film layer and comprising a dielectric plate provided with a plurality of recesses each provided with a film layer and holding a sample in contact with the film layer, and a reflecting optical system including a reflecting surface which is formed on the dielectric plate for each of the recesses to cause the light beam emitted from the light source to impinge upon the interface between the film layer of the recess and the dielectric plate and/or to cause the light beam reflected at the interface between the film layer of the recess and the dielectric plate to travel toward a predetermined position.

When the measuring plate in accordance with the present invention is to be used in a surface plasmon resonance sensor, the film layer of each of the recesses comprises a metal film, whereas when the measuring plate in accordance with the present invention is to be used in a leaky mode sensor, the film layer of each of the recesses comprises a clad layer and an optical waveguide layer formed on the clad layer.

In the measuring plate of the present invention, the reflecting optical system provided for each recess is for confining the light beam for measuring the sample in the recess within a predetermined area not to be interfered with recesses adjacent to the recess or elements for the recesses adjacent to the recess, and at the same time, it is preferred that the recesses be formed at substantially regular intervals.

In one embodiment, the dielectric plate is provided with a plurality of recesses, each having a flat and smooth bottom, on the upper side thereof, the film layer is formed on the bottom of each recess, and the reflecting optical system for each recess comprises a reflecting surface formed on the lower side of the dielectric plate to reflect a light beam impinging thereupon from below toward the interface between the film layer and the dielectric plate.

In another embodiment, the dielectric plate is provided with a plurality of recesses, each having a flat and smooth bottom, on the upper side thereof, the film layer is formed on the bottom of each recess, and the reflecting optical system for each recess comprises a reflecting surface formed on the lower side of the dielectric plate to reflect downward a light beam reflected at the interface between the film layer and the dielectric plate.

In still another embodiment, the dielectric plate is provided with a plurality of recesses, each having a flat and smooth bottom, on the upper side thereof, the film layer is formed on the bottom of each recess, and the reflecting optical system for each recess comprises a reflecting surface formed on the lower side of the dielectric plate to reflect a light beam impinging thereupon from above toward the interface between the film layer and the dielectric plate.

In still another embodiment, the dielectric plate is provided with a plurality of recesses, each having a flat and smooth bottom, on the upper side thereof, the film layer is formed on the bottom of each recess, and the reflecting optical system for each recess comprises a reflecting surface formed on the lower side of the dielectric plate to reflect upward a light beam reflected at the interface between the film layer and the dielectric plate.

In still another embodiment, the dielectric plate is provided with a plurality of recesses, each having a flat and smooth side surface, on the upper side thereof, the film layer is formed on the side surface of each recess, and the reflecting optical system for each recess comprises a reflecting surface formed on the upper side of the dielectric plate to reflect a light beam impinging thereupon from below toward the interface between the film layer and the dielectric plate.

In still another embodiment, the dielectric plate is provided with a plurality of recesses, each having a flat and smooth side surface, on the upper side thereof, the film layer is formed on the side surface of each recess, and the reflecting optical system for each recess comprises a reflecting surface formed on the upper side of the dielectric plate to reflect downward a light beam impinging upon the interface between the film layer and the dielectric plate from below and reflected at the interface.

In still another embodiment, the dielectric plate is provided with a plurality of recesses, each having a flat and smooth side surface, on the upper side thereof, the film layer is formed on the side surface of each recess, and the reflecting optical system for each recess comprises a reflecting surface formed on the lower side of the dielectric plate to reflect a light beam impinging thereupon from above toward the interface between the film layer and the dielectric plate.

In still another embodiment, the dielectric plate is provided with a plurality of recesses, each having a flat and smooth side surface, on the upper side thereof, the film layer is formed on the side surface of each recess, and the reflecting optical system for each recess comprises a reflecting surface formed on the lower side of the dielectric plate to reflect upward a light beam impinging upon the interface between the film layer and the dielectric plate from below and reflected at the interface.

It is preferred that the dielectric plate be formed of glass or transparent resin. It is further preferred that the dielectric plate be formed by one-piece injection molding.

It is further preferred that each of the recesses flares upward.

In the measuring plate of the present invention, since the reflecting optical system provided for each recess confines the light beam for measuring the sample in the recess within a predetermined area not to be interfered with recesses adjacent to the recess or elements for the recesses adjacent to the recess, the light beam for each recess cannot be eclipsed, for instance, by the bottom portion of recesses adjacent to the recess, and accordingly, the sample in each recess can be accurately analyzed.

BREIF DESCRIPTION OF THE DRWAINGS

Figure 2:
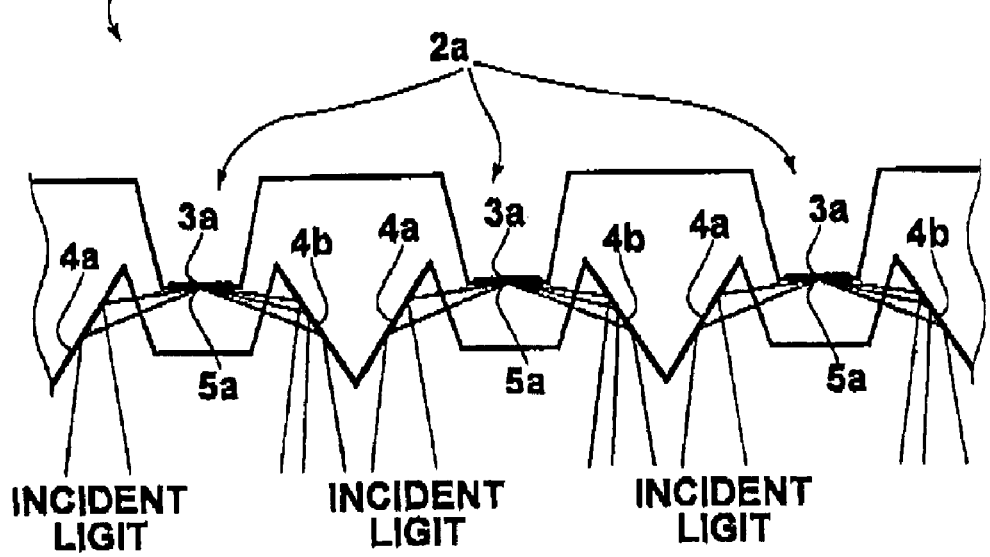
Figure 3:
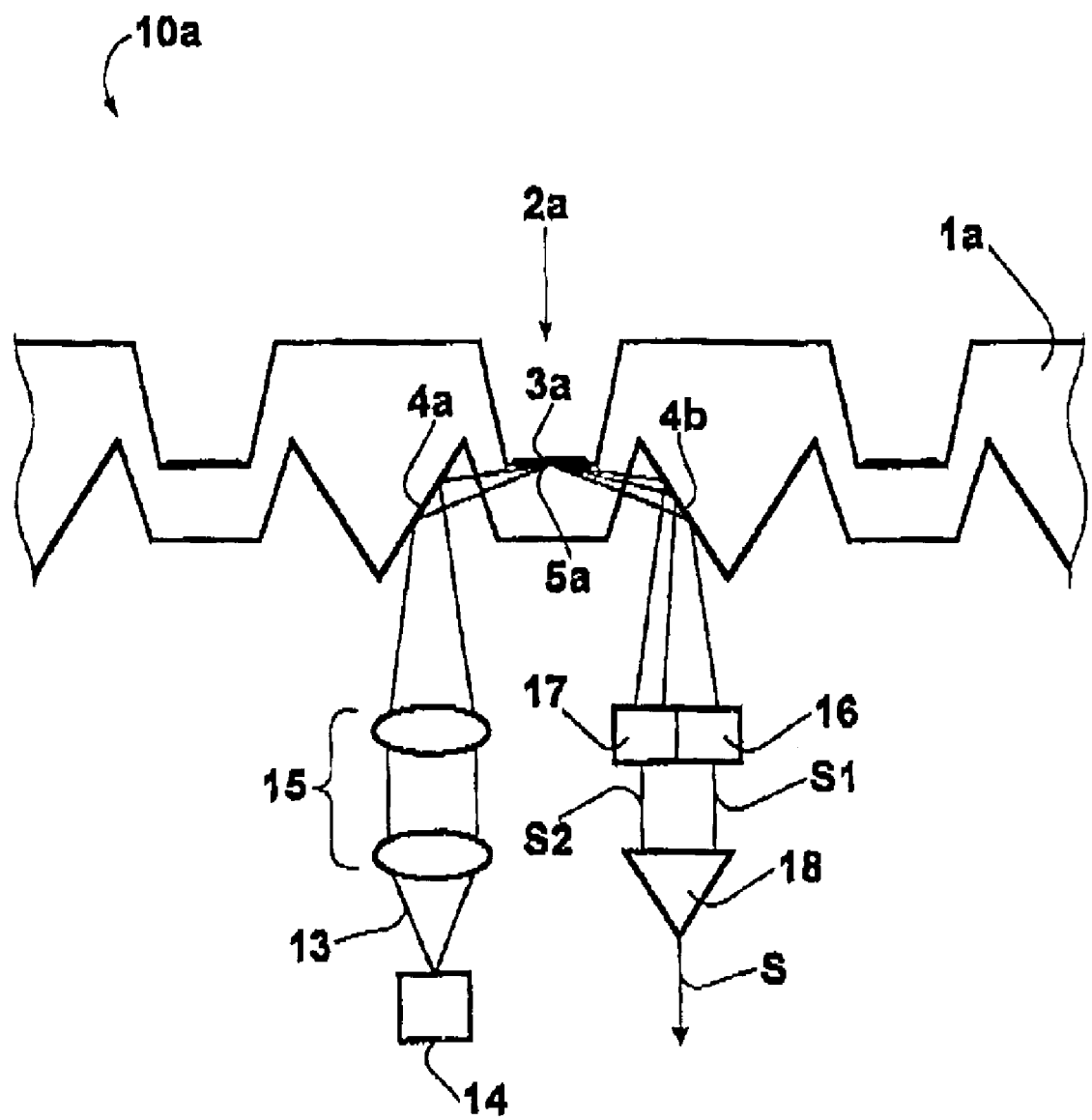
Figure 4A:
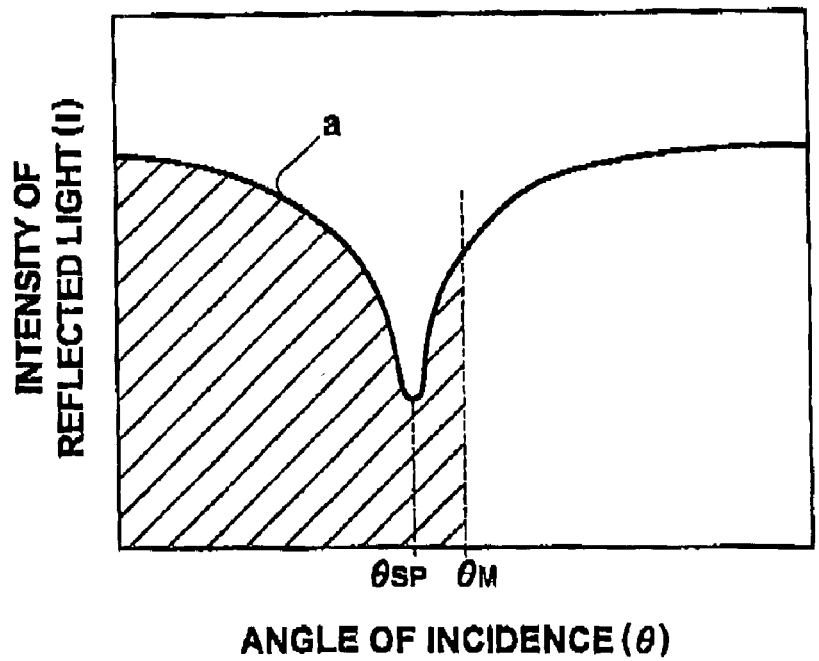
Figure 4B:
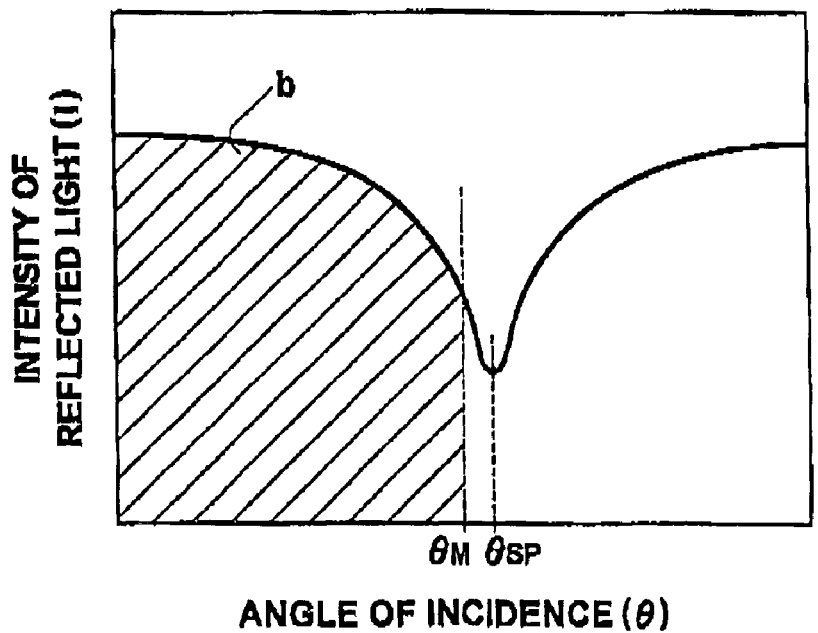
Figure 5:
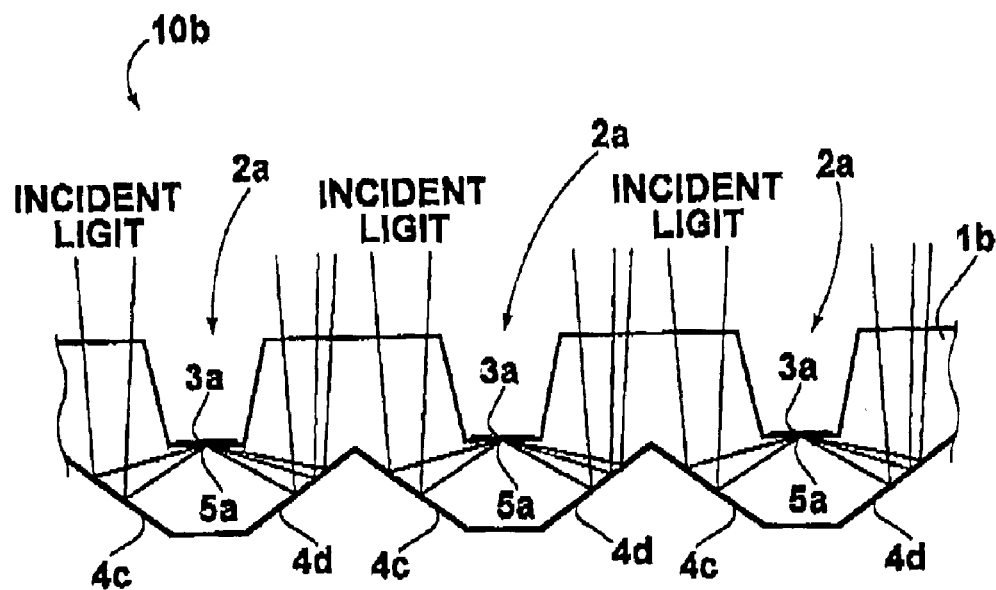
Figure 6:
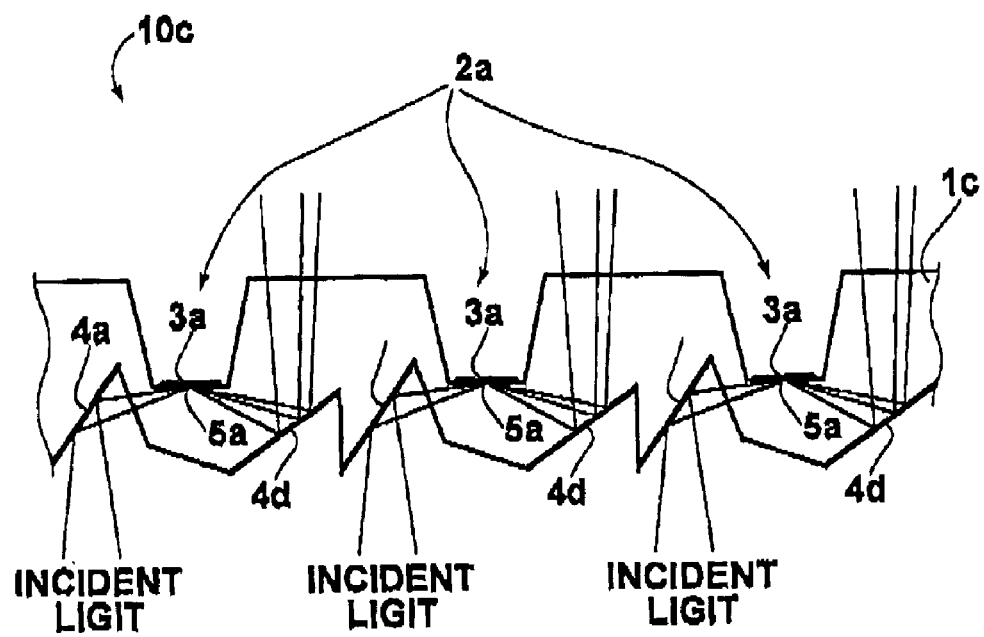
Figure 7:
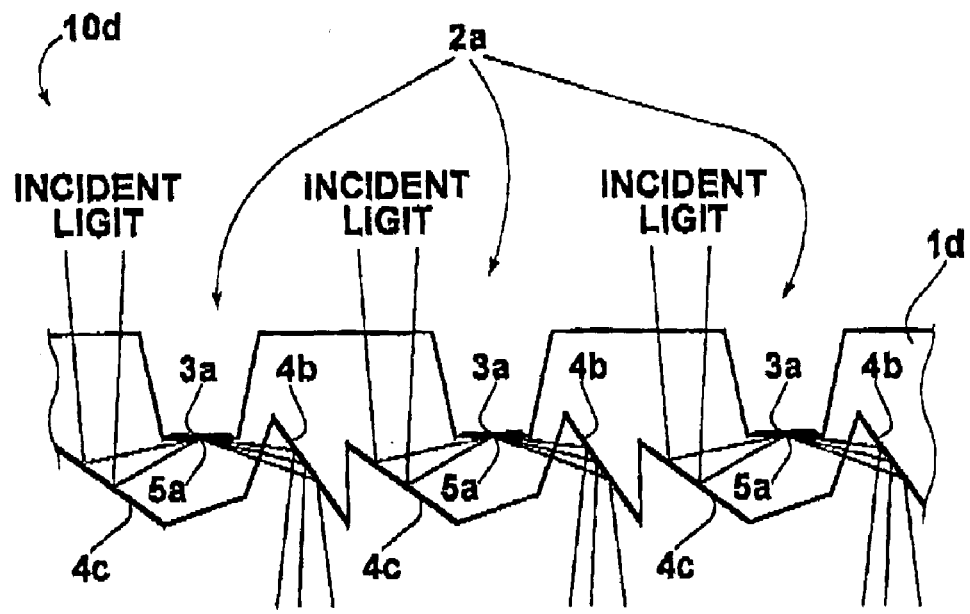
Figure 8:
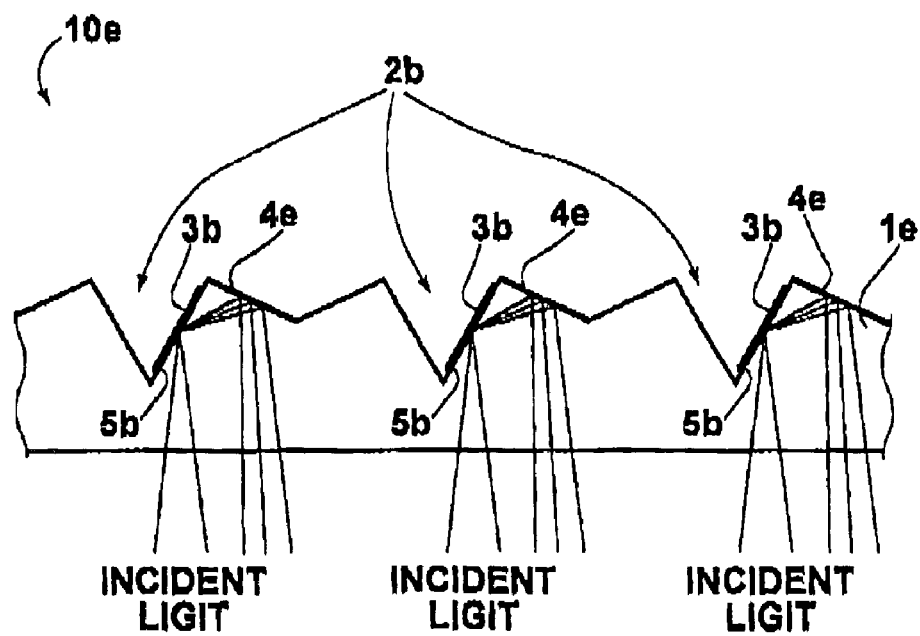
Figure 9:
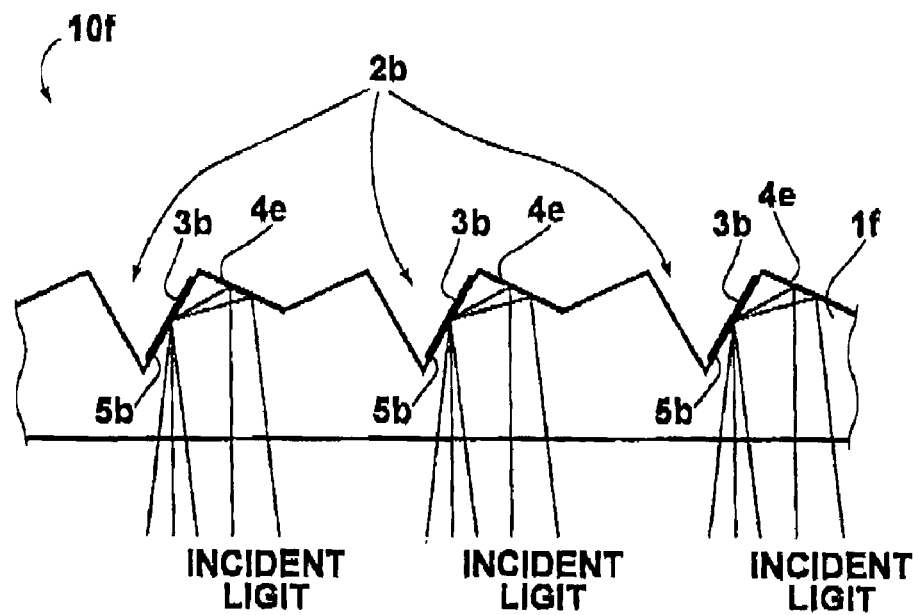
Figure 10:
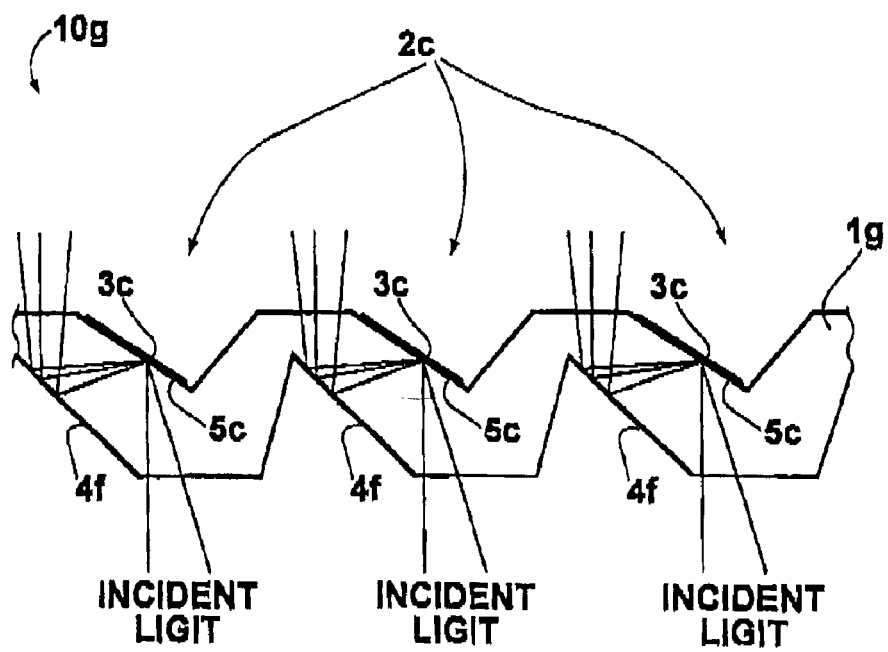
Figure 11:
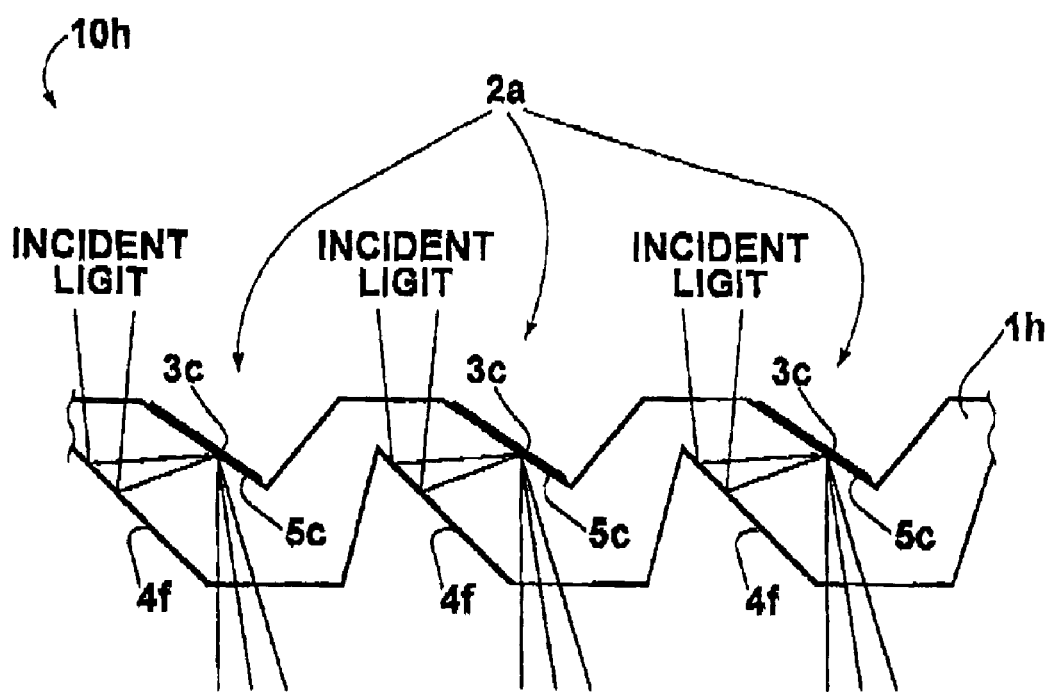

FIG. 1 is a perspective view of a measuring plate in accordance with a first embodiment of the present invention, FIG. 2 is a cross-sectional view taken along line A—A in FIG. 1, FIG. 3 is a fragmentary side view showing a part of a surface plasmon resonance sensor employing the measuring plate in accordance with the first embodiment of the present invention, FIGS. 4A and 4B are graphs showing the relation between the angle of incidence of light to the interface between the metal film and the dielectric plate and the intensity of the reflected light beam detected by the photodetector in the surface plasmon resonance sensor, FIG. 5 is a fragmentary cross-sectional view showing the measuring plate in accordance with a second embodiment of the present invention, FIG. 6 is a fragmentary cross-sectional view showing the measuring plate in accordance with a third embodiment of the present invention, FIG. 7 is a fragmentary cross-sectional view showing the measuring plate in accordance with a fourth embodiment of the present invention, FIG. 8 is a fragmentary cross-sectional view showing the measuring plate in accordance with a fifth embodiment of the present invention, FIG. 9 is a fragmentary cross-sectional view showing the measuring plate in accordance with a sixth embodiment of the present invention, FIG. 10 is a fragmentary cross-sectional view showing the measuring plate in accordance with a seventh embodiment of the present invention, and FIG. 11 is a fragmentary cross-sectional view showing the measuring plate in accordance with an eighth embodiment of the present invention.

DESCRIPTION OF THE PREFERRED EMBODIMENTS

FIG. 1 shows a measuring plate in accordance with a first embodiment of the present invention. The measuring plate of this embodiment is for a surface plasmon resonance sensor utilizing surface plasmon resonance.

In FIG. 1, the measuring plate 10a comprises a dielectric plate 1a of a dielectric material such as glass. A plurality of recesses 2a each functioning as a sample holder for storing therein a sample liquid are formed on the upper surface of the dielectric plate 1a. For example, each of the recesses 2a may be flared upward. The dielectric plate 1a may be of any size and the recesses 2a formed on the upper surface thereof may be any in number (e.g., 96, 384 or 1536) and may be arranged in any way.

The dielectric plate 1a may be easily produced by one-piece injection molding of, for instance, glass or transparent resin. As the transparent resin, PMMA, polycarbonate, amorphous polyolefin, or cycloolefin may be preferably employed. Generally it is preferred that the dielectric plate 1a be formed of a material which is 1.45 to 2.5 in refractive index since the surface plasmon resonance angle (the attenuation angle θsp) is practically obtained in the refractive index range.

As shown in FIG. 2, which is a cross-sectional view taken along line A—A in FIG. 1, the bottom surface of each recess 2a is flat and a metal film 3a, for instance, of gold, silver, copper, or aluminum, is provided on the flat bottom surface of each recess 2a. A reflecting optical system, comprising a mirror 4a which reflects a light beam, impinging thereupon from below, toward the interface 5a between the metal film 3a and the dielectric plate 1a and a mirror 4b which reflects downward the light beam reflected at the interface 5a, is provided on the lower side of the dielectric plate 1a for each of the recesses 2a. The metal films 3a and mirrors 4a and 4b can be formed by depositing metal in predetermined positions of the dielectric plate 1a.

The measuring plate 10a can be modified to a measuring plate for a leaky mode sensor by replacing the metal films 3a with a clad layer and an optical waveguide layer.

A surface plasmon resonance sensor employing the measuring plate 10a of this embodiment will be described, hereinbelow.

FIG. 3 shows a surface plasmon detecting portion of the surface plasmon resonance sensor.

As shown in FIG. 3, the surface plasmon resonance sensor comprises the measuring plate 10a, and the surface plasmon detecting portion. The surface plasmon detecting portion comprises a laser (e.g., a semiconductor laser) 14 which emits a light beam 13, an incident optical system 15 which causes the light beam 13 by way of the mirror 4a to impinge upon the interface 5a between the metal film 3a and the dielectric plate 1a at various angles of incidence, first and second photodetectors 16 and 17 which detect the amount of light beam 13 reflected at the interface 5a, and a comparator 18 connected to the first and second photodetectors 16 and 17.

In this particular embodiment, the laser 14, the incident optical system 15 and the photodetectors 16 and 17 are disposed below the measuring plate 10a and the light beam 13 reflected at the interface 5a to impinge upon the first and second photodetectors 16 and 17 by way of the mirror 4b is detected by the first and second photodetectors 16 and 17.

The incident optical system 15 comprises a collimator lens 15a which collimates the light beam 13 emitted from the laser 14 as a divergent light beam and a condenser lens 15b which converges the collimated light beam 13 on the interface 5a.

Since converged by the condenser lens 15b as described above, the laser beam 13 includes components impinging upon the interface at various angles of incidence θ. The laser 14 and the incident optical system 15 are arranged so that the angles of incidence θ are all not smaller than the angle of total internal reflection. Accordingly, the laser beam 13 is reflected in total internal reflection at the interface 5a and the reflected laser beam 13 includes components reflected at the interface 5a at various angles of reflection. The incident optical system 15 may be arranged to cause the laser beam 13 to impinge upon the interface 5a in a defocused state.

This arrangement averages errors in detecting states of surface plasmon resonance and improves measuring accuracy.

The laser beam 13 is caused to impinge upon the interface 5a in a p-polarized state. This can be realized by positioning the laser 14 so that the laser beam 13 impinges upon the interface 5a in a p-polarized state. Otherwise, the direction of polarization of the laser beam 13 may be controlled by a wavelength plate.

The first and second photodetectors 16 and 17 may comprise, for instance, a split photodiode. The first photodetector 16 is disposed to detect the amount of components of the light beam 13 in a first predetermined range (relatively small angle range) of angle of reflection and the second photodetector 17 is disposed to detect the amount of components of the light beam 13 in a second predetermined range (relatively large angle range) of angle of reflection.

Analysis of the sample by the surface plasmon resonance sensor will be described, hereinbelow. A samples is put in each of the recesses 2a of the measuring plate 10a to be held in contact with the metal film 3a in the recess 2a. A light beam 13 is converged on the interface 5a between the metal film 3a and the dielectric plate 1a and the light beam 13 reflected in total internal reflection at the interface 5a is detected by the first and second photodetectors 16 and 17. A first detecting signal S1 output from the first photodetector 16 representing the amount of light beam 13 impinging upon the first photodetector 16 is input into the comparator 18 and a second detecting signal S2 output from the second photodetector 17 representing the amount of light beam 13 impinging upon the second photodetector 17 is input into the comparator 18. The comparator 18 outputs a differential signal S representing the difference between the first and second detecting signals S1 and S2.

The component impinging upon the interface at a particular angle of incidence θsp excites the surface plasmon and the intensity I of light reflected in total internal reflection at the interface 5a sharply drops for this component. That is, the relation between the intensity I of the light beam 13 reflected in total internal reflection at the interface 5a and the angle of incidence θ is substantially as shown by curve a in FIG. 4A and by curve b in FIG. 4B. When the attenuation angle θsp and the curves representing the relation between the intensity I of the light beam 13 reflected in total internal reflection at the interface 5a and the angle of incidence θ are known, the specific material in the sample can be quantitatively analyzed. The reason for this will be described in detail, hereinbelow.

Assuming that the first and second predetermined ranges of angle of reflection are contiguous to each other on opposite sides of angle of reflection $\theta_M$, and the first photodetector 16 detects the components of the light beam 13 which impinges upon the interface Sa at an angle of incidence smaller than M, whereas the second photodetector 17 detects the components of the light beam 13 which impinges upon the interface Sa at an angle of incidence larger than $\theta_M$, the first photodetector 16 detects the components of the light beam 13 in the range represented by the hatched portion in FIGS. 4A and 4B and the amount of light detected by the first photodetector 16 is larger in the case shown by FIG. 4B than in the case shown by FIG. 4A. To the contrast, the amount of light detected by the second photodetector 17 is smaller in the case shown by FIG. 4B than in the case shown by FIG. 4A. Thus, the outputs of the first and second photodetectors 16 and 17 exhibit a specific difference according to the relation between the intensity I of the light beam 13 reflected in total internal reflection at the interface 5a and the angle of incidence θ.

Accordingly, the attenuation angle θsp, the curves representing the relation between the intensity I of the light beam 13 reflected in total internal reflection at the interface 5a and the angle of incidence θ and the like can be estimated on the basis of the output S of the comparator 18 (representing the difference between the first and second detecting signals S1 and S2) by referring to a calibration curve which has been prepared for each sample, whereby the specific material in the sample can be quantitatively analyzed.

Even if the first and second predetermined ranges of angle of reflection are not contiguous to each other, the outputs of the first and second photodetectors 16 and 17 exhibit a specific difference according to the relation between the intensity I of the light beam 13 reflected in total internal reflection at the interface 5a and the angle of incidence θ and accordingly, the specific material in the sample can be quantitatively analyzed in the same manner.

By linearly or two-dimensionally arranging a plurality of the surface plasmon detecting portions with each surface plasmon detecting portion opposed to one of the recesses 2a of the measuring plate 10a, samples in a plurality of recesses 2a can be simultaneously analyzed. Since the optical path of the light beam 13 for measuring the sample in each recess 2a is confined within the space between adjacent recesses 2a, the light beam 13 for each recess 2a cannot be eclipsed, for instance, by the bottom portion of recesses 2a adjacent to the recess 2a, and accordingly, the sample in each recess 2a can be accurately analyzed.

A measuring plate in accordance with a second embodiment of the present invention will be described with reference to FIG. 5, hereinbelow. In FIG. 5, elements analogous to those shown in FIGS. 1 and 2 are given the same reference numerals and will not be described here unless necessary.

In FIG. 5, the measuring plate 10b in accordance with the second embodiment comprises a dielectric plate 1b and a plurality of recesses 2a are formed on the upper surface of the dielectric plate 1b. The bottom surface of each recess 2a is flat and a metal film 3a, for instance, of gold, silver, copper, or aluminum, is provided on the flat bottom surface of each recess 2a. A reflecting optical system, comprising a mirror 4c which reflects a light beam, impinging thereupon from above, toward the interface Sa between the metal film 3a and the dielectric plate 1b and a mirror 4d which reflects upward the light beam reflected at the interface 5a, is provided on the lower side of the dielectric plate 1b for each of the recesses 2a.

In this particular embodiment, the laser 14, the incident optical system 15 and the photodetectors 16 and 17 are disposed above the measuring plate 10b and the light beam 13 reflected at the interface Sa to impinge upon the first and second photodetectors 16 and 17 by way of the mirror 4d is detected by the first and second photodetectors 16 and 17.

With this embodiment, result similar to that obtained with the first embodiment can be obtained.

A measuring plate in accordance with a third embodiment of the present invention will be described with reference to FIG. 6, hereinbelow. In FIG. 6, elements analogous to those shown in FIGS. 1 and 2 are given the same reference numerals and will not be described here unless necessary.

In FIG. 6, the measuring plate 10c in accordance with the third embodiment comprises a dielectric plate 1c and a plurality of recesses 2a are formed on the upper surface of the dielectric plate 1c. The bottom surface of each recess 2a is flat and a metal film 3a, for instance, of gold, silver, copper, or aluminum, is provided on the flat bottom surface of each recess 2a. A reflecting optical system, comprising a mirror 4a which reflects a light beam, impinging thereupon from below, toward the interface 5a between the metal film 3a and the dielectric plate 1c and a mirror 4d which reflects upward the light beam reflected at the interface 5a, is provided on the lower side of the dielectric plate 1b for each of the recesses 2a.

In this particular embodiment, the laser 14 and the incident optical system 15 are disposed below the measuring plate 10c with the first and second photodetectors 16 and 17 disposed above the measuring plate 10c and the light beam 13 reflected at the interface 5a to impinge upon the first and second photodetectors 16 and 17 by way of the mirror 4d is detected by the first and second photodetectors 16 and 17.

With this embodiment, result similar to that obtained with the first embodiment can be obtained.

A measuring plate in accordance with a fourth embodiment of the present invention will be described with reference to FIG. 7, hereinbelow. In FIG. 7, elements analogous to those shown in FIGS. 1 and 2 are given the same reference numerals and will not be described here unless necessary.

In FIG. 7, the measuring plate 10d in accordance with the fourth embodiment comprises a dielectric plate 1d and a plurality of recesses 2a are formed on the upper surface of the dielectric plate 1d. The bottom surface of each recess 2a is flat and a metal film 3a, for instance, of gold, silver, copper, or aluminum, is provided on the flat bottom surface of each recess 2a. A reflecting optical system, comprising a mirror 4c which reflects a light beam, impinging thereupon from above, toward the interface 5a between the metal film 3a and the dielectric plate 1d and a mirror 4b which reflects downward the light beam reflected at the interface 5a, is provided on the lower side of the dielectric plate 1d for each of the recesses 2a.

In this particular embodiment, the laser 14 and the incident optical system 15 are disposed above the measuring plate 10d with the first and second photodetectors 16 and 17 disposed below the measuring plate 10d and the light beam 13 reflected at the interface 5a to impinge upon the first and second photodetectors 16 and 17 by way of the mirror 4b is detected by the first and second photodetectors 16 and 17.

With this embodiment, result similar to that obtained with the first embodiment can be obtained.

A measuring plate in accordance with a fifth embodiment of the present invention will be described with reference to FIG. 8, hereinbelow. In FIG. 8, elements analogous to those shown in FIGS. 1 and 2 are given the same reference numerals and will not be described here unless necessary.

In FIG. 8, the measuring plate 10e in accordance with the fifth embodiment comprises a dielectric plate 1e and a plurality of recesses 2b are formed on the upper surface of the dielectric plate 1e. A side surface of each recess 2b is flat and a metal film 3b, for instance, of gold, silver, copper, or aluminum, is provided on the flat side surface of each recess 2b. A reflecting optical system, comprising a mirror 4e which reflects downward a light beam, impinging upon the interface 5b between the metal film 3b and the dielectric plate 1e from below and reflected at the interface 5b, is provided on the upper side of the dielectric plate 1e for each of the recesses 2b.

In this particular embodiment, the laser 14, the incident optical system 15 and the first and second photodetectors 16 and 17 are disposed below the measuring plate 10e and the light beam 13 reflected at the interface 5b to impinge upon the first and second photodetectors 16 and 17 by way of the mirror 4e is detected by the first and second photodetectors 16 and 17.

With this embodiment, result similar to that obtained with the first embodiment can be obtained.

A measuring plate in accordance with a sixth embodiment of the present invention will be described with reference to FIG. 9, hereinbelow. In FIG. 9, elements analogous to those shown in FIGS. 1 and 2 are given the same reference numerals and will not be described here unless necessary.

In FIG. 9, the measuring plate 10f in accordance with the sixth embodiment comprises a dielectric plate 1f and a plurality of recesses 2b are formed on the upper surface of the dielectric plate 1f. A side surface of each recess 2b is flat and a metal film 3b, for instance, of gold, silver, copper, or aluminum, is provided on the flat side surface of each recess 2b. A reflecting optical system, comprising a mirror 4e which reflects a light beam, impinging thereupon from below, toward the interface 5b between the metal film 3b and the dielectric plate 1f, is provided on the upper side of the dielectric plate 1f for each of the recesses 2b.

In this embodiment, the laser 14, the incident optical system 15 and the first and second photodetectors 16 and 17 are disposed below the measuring plate 10f and the light beam 13 reflected downward at the interface 5b to impinge upon the first and second photodetectors 16 and 17 is detected by the first and second photodetectors 16 and 17.

With this embodiment, result similar to that obtained with the first embodiment can be obtained.

A measuring plate in accordance with a seventh embodiment of the present invention will be described with reference to FIG. 10, hereinbelow. In FIG. 10, elements analogous to those shown in FIGS. 1 and 2 are given the same reference numerals and will not be described here unless necessary.

In FIG. 10, the measuring plate 10g in accordance with the seventh embodiment comprises a dielectric plate 1g and a plurality of recesses 2c are formed on the upper surface of the dielectric plate 1g. A side surface of each recess 2c is flat and a metal film 3c, for instance, of gold, silver, copper, or aluminum, is provided on the flat side surface of each recess 2c. A reflecting optical system, comprising a mirror 4f which reflects upward a light beam, impinging upon the interface 5c between the metal film 3c and the dielectric plate 1g from below and reflected at the interface 5b, is provided on the lower side of the dielectric plate 1g for each of the recesses 2c.

In this embodiment, the laser 14 and the incident optical system 15 are disposed below the measuring plate 10g with the first and second photodetectors 16 and 17 disposed above the measuring plate 10g and the light beam 13 reflected at the interface 5c to impinge upon the first and second photodetectors 16 and 17 by way of the mirror 4f is detected by the first and second photodetectors 16 and 17.

With this embodiment, result similar to that obtained with the first embodiment can be obtained.

A measuring plate in accordance with an eighth embodiment of the present invention will be described with reference to FIG. 11, hereinbelow. In FIG. 11, elements analogous to those shown in FIGS. 1 and 2 are given the same reference numerals and will not be described here unless necessary.

In FIG. 11, the measuring plate 10h in accordance with the eighth embodiment comprises a dielectric plate 1h and a plurality of recesses 2c are formed on the upper surface of the dielectric plate 1h. A side surface of each recess 2c is flat and a metal film 3c, for instance, of gold, silver, copper, or aluminum, is provided on the flat side surface of each recess

2c. A reflecting optical system, comprising a mirror 4f which reflects a light beam, impinging thereupon from above, toward the interface 5c between the metal film 3c and the dielectric plate 1h, is provided on the lower side of the dielectric plate 1h for each of the recesses 2c.

In this particular embodiment, the laser 14 and the incident optical system 15 are disposed above the measuring plate 10h with the first and second photodetectors 16 and 17 disposed below the measuring plate 10h and the light beam 13 reflected at the interface 5c to impinge upon the first and second photodetectors 16 and 17 by way of the mirror 4f is detected by the first and second photodetectors 16 and 17.

With this embodiment, result similar to that obtained with the first embodiment can be obtained.

What is claimed is:

1. A measuring plate for use in a sensor utilizing the phenomenon of attenuation in total internal reflection comprising a dielectric block provided with a film layer to be brought into contact with a sample, a light source which emits a light beam, an incident optical system which causes the light beam to enter the dielectric block so that total internal reflection conditions are satisfied at the interface of the dielectric block and the film layer and various angles of incidence of the light beam to the interface can be obtained, and a photodetector means which detects the intensity of the light beam reflected in total internal reflection at the interface and detects a state of attenuation in total internal reflection, the measuring plate being for providing the dielectric block and the film layer and comprising a dielectric plate provided with a plurality of recesses each provided with a film layer and holding a sample in contact with the film layer, and a reflecting optical system including a reflecting surface which is formed on the dielectric plate for each of the recesses to cause the light beam emitted from the light source to impinge upon the interface between the film layer of the recess and the dielectric plate and/or to cause the light beam reflected at the interface between the film layer of the recess and the dielectric plate to travel toward a predetermined position.

2. A measuring plate as defined in claim 1 in which the dielectric plate is formed of glass or transparent resin.

3. A measuring plate as defined in claim 1 in which the dielectric plate is provided with a plurality of recesses, each having a flat and smooth bottom, on the upper side thereof, the film layer is formed on the bottom of each recess, and the reflecting optical system for each recess comprises a reflecting surface formed on the lower side of the dielectric plate to reflect a light beam impinging thereupon from below toward the interface between the film layer and the dielectric plate.

4. A measuring plate as defined in claim 1 in which the dielectric plate is provided with a plurality of recesses, each having a flat and smooth bottom, on the upper side thereof, the film layer is formed on the bottom of each recess, and the reflecting optical system for each recess comprises a reflecting surface formed on the lower side of the dielectric plate to reflect downward a light beam reflected at the interface between the film layer and the dielectric plate.

5. A measuring plate as defined in claim 1 in which the dielectric plate is provided with a plurality of recesses, each having a flat and smooth bottom, on the upper side thereof, the film layer is formed on the bottom of each recess, and the reflecting optical system for each recess comprises a reflecting surface formed on the lower side of the dielectric plate to reflect a light beam impinging thereupon from above toward the interface between the film layer and the dielectric plate.

6. A measuring plate as defined in claim 1 in which the dielectric plate is provided with a plurality of recesses, each having a flat and smooth bottom, on the upper side thereof, the film layer is formed on the bottom of each recess, and the reflecting optical system for each recess comprises a reflecting surface formed on the lower side of the dielectric plate to reflect upward a light beam reflected at the interface between the film layer and the dielectric plate.

7. A measuring plate as defined in claim 1 in which the dielectric plate is provided with a plurality of recesses, each having a flat and smooth side surface, on the upper side thereof, the film layer is formed on the side surface of each recess, and the reflecting optical system for each recess comprises a reflecting surface formed on the upper side of the dielectric plate to reflect a light beam impinging thereupon from below toward the interface between the film layer and the dielectric plate.

8. A measuring plate as defined in claim 1 in which the dielectric plate is provided with a plurality of recesses, each having a flat and smooth side surface, on the upper side thereof, the film layer is formed on the side surface of each recess, and the reflecting optical system for each recess comprises a reflecting surface formed on the upper side of the dielectric plate to reflect downward a light beam impinging upon the interface between the film layer and the dielectric plate from below and reflected at the interface.

9. A measuring plate as defined in claim 1 in which the dielectric plate is provided with a plurality of recesses, each having a flat and smooth side surface, on the upper side thereof, the film layer is formed on the side surface of each recess, and the reflecting optical system for each recess comprises a reflecting surface formed on the lower side of the dielectric plate to reflect a light beam impinging thereupon from above toward the interface between the film layer and the dielectric plate.

10. A measuring plate as defined in claim 1 in which the dielectric plate is provided with a plurality of recesses, each having a flat and smooth side surface, on the upper side thereof, the film layer is formed on the side surface of each recess, and the reflecting optical system for each recess comprises a reflecting surface formed on the lower side of the dielectric plate to reflect upward a light beam impinging upon the interface between the film layer and the dielectric plate from below and reflected at the interface.

11. A measuring plate for use in a sensor utilizing the phenomenon of attenuation in total internal reflection comprising a dielectric block provided with a metal film to be brought into contact with a sample, a light source which emits a light beam, an incident optical system which causes the light beam to enter the dielectric block so that total internal reflection conditions are satisfied at the interface of the dielectric block and the metal film and various angles of incidence of the light beam to the interface can be obtained, and a photodetector means which detects the intensity of the light beam reflected in total internal reflection at the interface and detects a state of attenuation in total internal reflection, the measuring plate being for providing the dielectric block and the metal film and comprising a dielectric plate provided with a plurality of recesses each provided with a metal film and holding a sample in contact with the metal film, and a reflecting optical system including a reflecting surface which is formed on the dielectric plate for each of the recesses to cause the light beam emitted from the light source to impinge upon the interface between the metal film of the recess and the dielectric plate and/or to cause the light beam reflected at the interface between the metal film of the recess and the dielectric plate to travel toward a predetermined position.

12. A measuring plate as defined in claim 11 in which the dielectric plate is formed of glass or transparent resin.

13. A measuring plate as defined in claim 11 in which the dielectric plate is provided with a plurality of recesses, each having a flat and smooth bottom, on the upper side thereof, the metal film is formed on the bottom of each recess, and the reflecting optical system for each recess comprises a reflecting surface formed on the lower side of the dielectric plate to reflect a light beam impinging thereupon from below toward the interface between the metal film and the dielectric plate.

14. A measuring plate as defined in claim 11 in which the dielectric plate is provided with a plurality of recesses, each having a flat and smooth bottom, on the upper side thereof, the metal film is formed on the bottom of each recess, and the reflecting optical system for each recess comprises a reflecting surface formed on the lower side of the dielectric plate to reflect downward a light beam reflected at the interface between the metal film and the dielectric plate.

15. A measuring plate as defined in claim 11 in which the dielectric plate is provided with a plurality of recesses, each having a flat and smooth bottom, on the upper side thereof, the metal film is formed on the bottom of each recess, and the reflecting optical system for each recess comprises a reflecting surface formed on the lower side of the dielectric plate to reflect a light beam impinging thereupon from above toward the interface between the metal film and the dielectric plate.

16. A measuring plate as defined in claim 11 in which the dielectric plate is provided with a plurality of recesses, each having a flat and smooth bottom, on the upper side thereof, the metal film is formed on the bottom of each recess, and the reflecting optical system for each recess comprises a reflecting surface formed on the lower side of the dielectric plate to reflect upward a light beam reflected at the interface between the metal film and the dielectric plate.

17. A measuring plate as defined in claim 11 in which the dielectric plate is provided with a plurality of recesses, each having a flat and smooth side surface, on the upper side thereof, the metal film is formed on the side surface of each recess, and the reflecting optical system for each recess comprises a reflecting surface formed on the upper side of the dielectric plate to reflect a light beam impinging thereupon from below toward the interface between the metal film and the dielectric plate.

18. A measuring plate as defined in claim 11 in which the dielectric plate is provided with a plurality of recesses, each having a flat and smooth side surface, on the upper side thereof, the metal film is formed on the side surface of each recess, and the reflecting optical system for each recess comprises a reflecting surface formed on the upper side of the dielectric plate to reflect downward a light beam impinging upon the interface between the metal film and the dielectric plate from below and reflected at the interface.

19. A measuring plate as defined in claim 11 in which the dielectric plate is provided with a plurality of recesses, each having a flat and smooth side surface, on the upper side thereof, the metal film is formed on the side surface of each recess, and the reflecting optical system for each recess comprises a reflecting surface formed on the lower side of the dielectric plate to reflect a light beam impinging thereupon from above toward the interface between the metal film and the dielectric plate.

20. A measuring plate as defined in claim 11 in which the dielectric plate is provided with a plurality of recesses, each having a flat and smooth side surface, on the upper side thereof, the metal film is formed on the side surface of each recess, and the reflecting optical system for each recess comprises a reflecting surface formed on the lower side of the dielectric plate to reflect upward a light beam impinging upon the interface between the metal film and the dielectric plate from below and reflected at the interface.

21. A measuring plate for use in a sensor utilizing the phenomenon of attenuation in total internal reflection comprising a dielectric block provided with a clad layer and an optical waveguide layer formed on the clad layer to be brought into contact with a sample, a light source which emits a light beam, an incident optical system which causes the light beam to enter the dielectric block so that total internal reflection conditions are satisfied at the interface of the dielectric block and the clad layer and various angles of incidence of the light beam to the interface can be obtained, and a photodetector means which detects the intensity of the light beam reflected in total internal reflection at the interface and detects a state of attenuation in total internal reflection, the measuring plate being for providing the dielectric block, the clad layer and the optical waveguide layer, and comprising a dielectric plate provided with a plurality of recesses each provided with a clad layer and an optical waveguide layer and holding a sample in contact with the film layer, and a reflecting optical system including a reflecting surface which is formed on the dielectric plate for each of the recesses to cause the light beam emitted from the light source to impinge upon the interface between the clad layer of the recess and the dielectric plate and/or to cause the light beam reflected at the interface between the clad layer of the recess and the dielectric plate to travel toward a predetermined position.

22. A measuring plate as defined in claim 21 in which the dielectric plate is formed of glass or transparent resin.

23. A measuring plate as defined in claim 21 in which the dielectric plate is provided with a plurality of recesses, each having a flat and smooth bottom, on the upper side thereof, the clad layer and the optical waveguide layer are formed on the bottom of each recess, and the reflecting optical system for each recess comprises a reflecting surface formed on the lower side of the dielectric plate to reflect a light beam impinging thereupon from below toward the interface between the clad layer and the dielectric plate.

24. A measuring plate as defined in claim 21 in which the dielectric plate is provided with a plurality of recesses, each having a flat and smooth bottom, on the upper side thereof, the clad layer and the optical waveguide layer are formed on the bottom of each recess, and the reflecting optical system for each recess comprises a reflecting surface formed on the lower side of the dielectric plate to reflect downward a light beam reflected at the interface between the clad layer and the dielectric plate.

25. A measuring plate as defined in claim 21 in which the dielectric plate is provided with a plurality of recesses, each having a flat and smooth bottom, on the upper side thereof, the clad layer and the optical waveguide layer are formed on the bottom of each recess, and the reflecting optical system for each recess comprises a reflecting surface formed on the lower side of the dielectric plate to reflect a light beam impinging thereupon from above toward the interface between the clad layer and the dielectric plate.

26. A measuring plate as defined in claim 21 in which the dielectric plate is provided with a plurality of recesses, each having a flat and smooth bottom, on the upper side thereof, the clad layer and the optical waveguide layer are formed on the bottom of each recess, and the reflecting optical system for each recess comprises a reflecting surface formed on the lower side of the dielectric plate to reflect upward a light beam reflected at the interface between the clad layer and the dielectric plate.

27. A measuring plate as defined in claim 21 in which the dielectric plate is provided with a plurality of recesses, each having a flat and smooth side surface, on the upper side thereof, the clad layer and the optical waveguide layer are formed on the side surface of each recess, and the reflecting optical system for each recess comprises a reflecting surface formed on the upper side of the dielectric plate to reflect a light beam impinging thereupon from below toward the interface between the clad layer and the dielectric plate.

28. A measuring plate as defined in claim 21 in which the dielectric plate is provided with a plurality of recesses, each having a flat and smooth side surface, on the upper side thereof, the clad layer and the optical waveguide layer are formed on the side surface of each recess, and the reflecting optical system for each recess comprises a reflecting surface formed on the upper side of the dielectric plate to reflect downward a light beam impinging upon the interface between the clad layer and the dielectric plate from below and reflected at the interface.

29. A measuring plate as defined in claim 21 in which the dielectric plate is provided with a plurality of recesses, each having a flat and smooth side surface, on the upper side thereof, the clad layer and the optical waveguide layer are formed on the side surface of each recess, and the reflecting optical system for each recess comprises a reflecting surface formed on the lower side of the dielectric plate to reflect a light beam impinging thereupon from above toward the interface between the clad layer and the dielectric plate.

30. A measuring plate as defined in claim 21 in which the dielectric plate is provided with a plurality of recesses, each having a flat and smooth side surface, on the upper side thereof, the clad layer and the optical waveguide layer are formed on the side surface of each recess, and the reflecting optical system for each recess comprises a reflecting surface formed on the lower side of the dielectric plate to reflect upward a light beam impinging upon the interface between the clad layer and the dielectric plate from below and reflected at the interface.

* * * * *